United States Patent
Hsieh et al.

(10) Patent No.: US 6,775,347 B2
(45) Date of Patent: Aug. 10, 2004

(54) METHODS AND APPARATUS FOR RECONSTRUCTING AN IMAGE OF AN OBJECT

(75) Inventors: Jiang Hsieh, Brookfield, WI (US); Roy Arnulf Helge Nilsen, Menomonee Falls, WI (US); Mukta C. Joshi, Natick, MA (US); Sandeep Dutta, Waukesha, WI (US); Robert Wolfe, South Milwaukee, WI (US); John A. Fusco, Waukesha, WI (US); Ferry Tamtoro, New Berlin, WI (US)

(73) Assignee: GE Medical Systems Global Technology Company, Waukesha, WI (US)

( * ) Notice: Subject to any disclaimer, the term of this patent is extended or adjusted under 35 U.S.C. 154(b) by 189 days.

(21) Appl. No.: 10/158,690

(22) Filed: May 29, 2002

(65) Prior Publication Data
US 2003/0223533 A1 Dec. 4, 2003

(51) Int. Cl.[7] .............................................. A61B 6/03
(52) U.S. Cl. ........................................ 378/15; 378/901
(58) Field of Search ......................... 378/4, 8, 15, 19, 378/901

(56) References Cited

U.S. PATENT DOCUMENTS

| | | | | |
|---|---|---|---|---|
| 5,796,803 A | * | 8/1998 | Flohr et al. | 378/15 |
| 5,828,718 A | * | 10/1998 | Ruth et al. | 378/19 |
| 5,848,117 A | * | 12/1998 | Urchuk et al. | 378/19 |
| 6,078,639 A | | 6/2000 | Heuscher | |
| 6,173,032 B1 | | 1/2001 | Besson | |
| 6,233,308 B1 | | 5/2001 | Hsieh | |
| 6,246,742 B1 | | 6/2001 | Besson et al. | |
| 6,272,200 B1 | * | 8/2001 | Pan et al. | 378/15 |
| 6,324,241 B1 | | 11/2001 | Besson | |

* cited by examiner

*Primary Examiner*—David V Bruce
(74) *Attorney, Agent, or Firm*—Carl B. Horton, Esq.; Armstrong Teasdale LLP

(57) ABSTRACT

A method for reconstructing an image of an object includes generating a plurality of projection data, helically interpolating the projection data, rebinning the helically interpolated projection data from a fan-beam format to a parallel-beam format, and reconstructing an image of the object using the parallel-beam format projection data.

35 Claims, 5 Drawing Sheets

METHODS AND APPARATUS FOR RECONSTRUCTING AN IMAGE OF AN OBJECT

BACKGROUND OF THE INVENTION

This invention relates generally to computed tomographic (CT) imaging, and more particularly to methods and apparatus for operating a CT radiation source.

At least one known CT imaging system uses a fan-beam based helical algorithm to generate images that may include a significant noise in-homogeneity and an increased noise level. The noise in-homogeneity is mainly caused by an interaction between the helical weighting and a weighting factor in a fan beam backprojection. The noise variation within the scan field of view can vary more than a factor of two, even for a homogeneous scanned object. The noise in-homogeneity can increase away from an iso-center and may also generate image artifacts, such as Venetian blinds or zebra, in the three-dimensional reformatted images.

BRIEF DESCRIPTION OF THE INVENTION

In one aspect, a method for reconstructing an image of an object is provided. The method includes generating a plurality of projection data, helically interpolating the projection data, rebinning the helically interpolated projection data from a fan-beam format to a parallel-beam format, and reconstructing an image of the object using the parallel-beam format projection data.

In another aspect, a method for reconstructing an image of an object is provided. The method includes generating a plurality of projection data, helically interpolating the projection data, rebinning a first set of original measured projections wherein an angular increment between at least two views is uniform, rebinning a first set of interpolated projections wherein the angular increment between at least two views is uniform, and combining the first set of original measured projections and the first set of interpolated projections to reconstruct an image of an object.

In still another aspect, a method for reconstructing an image of an object is provided. The method includes rebinning a first set of original measured projections wherein an angular increment between at least two views is uniform, rebinning a first set of interpolated projections wherein the angular increment between at least two views is uniform, and combining the first set of original measured projections and the first set of interpolated projections to reconstruct an image of an object.

In yet another aspect, a computed tomographic (CT) imaging system for reconstructing an image of an object is provided. The CT system includes a radiation source, a detector array, and a computer coupled to the detector array and the radiation source. The computer is configured to generate a plurality of projection data, helically interpolate the projection data, rebin the helically interpolated projection data from a fan-beam format to a parallel-beam format, and reconstruct an image of the object using the parallel-beam format projection data.

In yet still another aspect, a computed tomographic (CT) imaging system for reconstructing an image of an object is provided. The CT system includes a radiation source, a detector array, and a computer coupled to the detector array and the radiation source. The computer is configured to generate a plurality of projection data, helically interpolate the projection data, rebin a first set of original measured projections wherein an angular increment between at least two views is uniform, rebin a first set of interpolated projections wherein the angular increment between at least two views is uniform, and combine the first set of original measured projections and the first set of interpolated projections to reconstruct an image of an object.

In still yet another aspect, a computer readable medium encoded with a program executable by a computer for reconstructing an image of an object is provided. The program is configured to instruct the computer to generate a plurality of projection data, helically interpolate the projection data, rebin the helically interpolated projection data from a fan-beam format to a parallel-beam format, and reconstruct an image of the object using the parallel-beam format projection data.

In still yet another aspect, a computer readable medium encoded with a program executable by a computer for reconstructing an image of an object is provided. The program is configured to instruct the computer to generate a plurality of projection data, helically interpolate the projection data, rebin a first set of original measured projections wherein an angular increment between at least two views is uniform, rebin a first set of interpolated projections wherein the angular increment between at least two views is uniform, and combine the first set of original measured projections and the first set of interpolated projections to reconstruct an image of an object.

DETAILED DESCRIPTION OF THE INVENTION

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
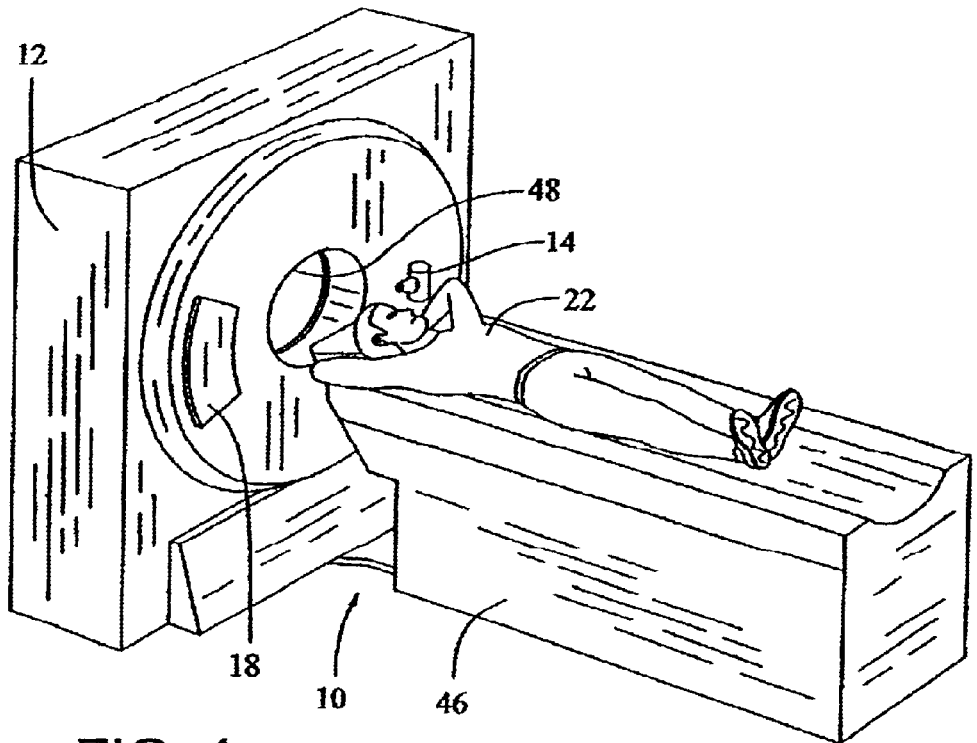
FIG. 1 is a pictorial view of a CT imaging system.
Figure 2:
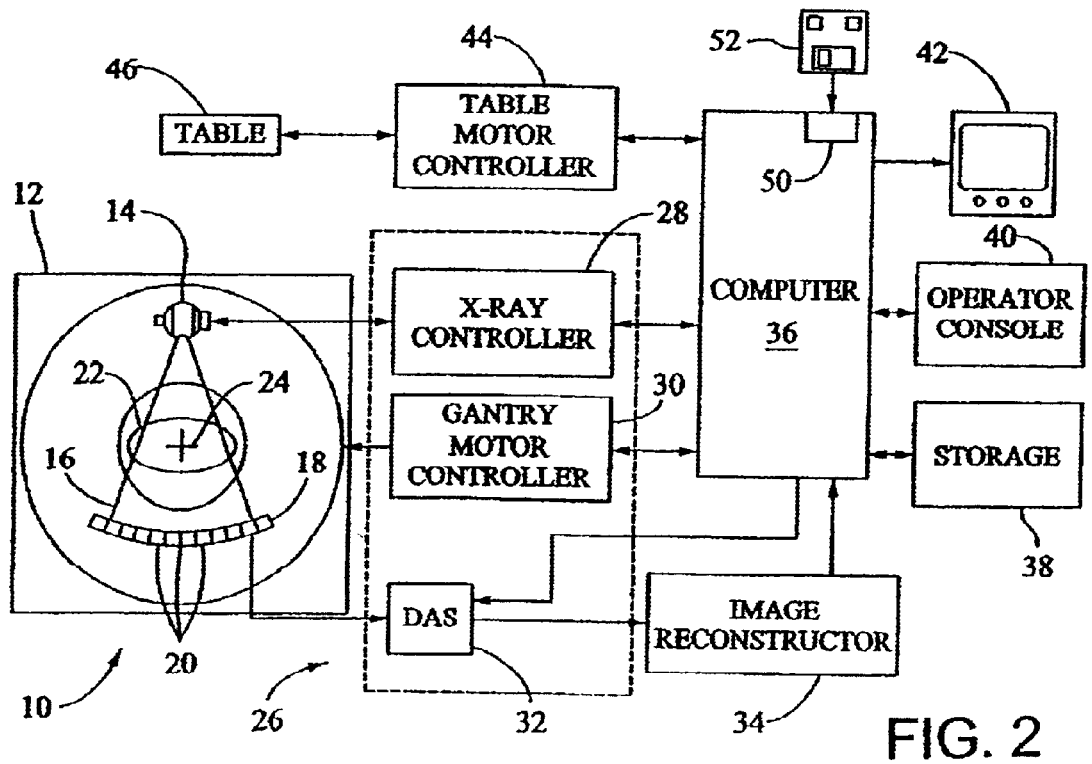
FIG. 2 is a block schematic diagram of the system illustrated in FIG. 2.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12. In one embodiment, radiation source 14 is a two-dimensional radiation source that projects a plurality of cone beams 16 from a plurality of locations on radiation source 14, also referred to herein as spots, on radiation source 14, toward detector 18 such that an inverted-cone beam geometry is received by detector 18.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes an radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 3:
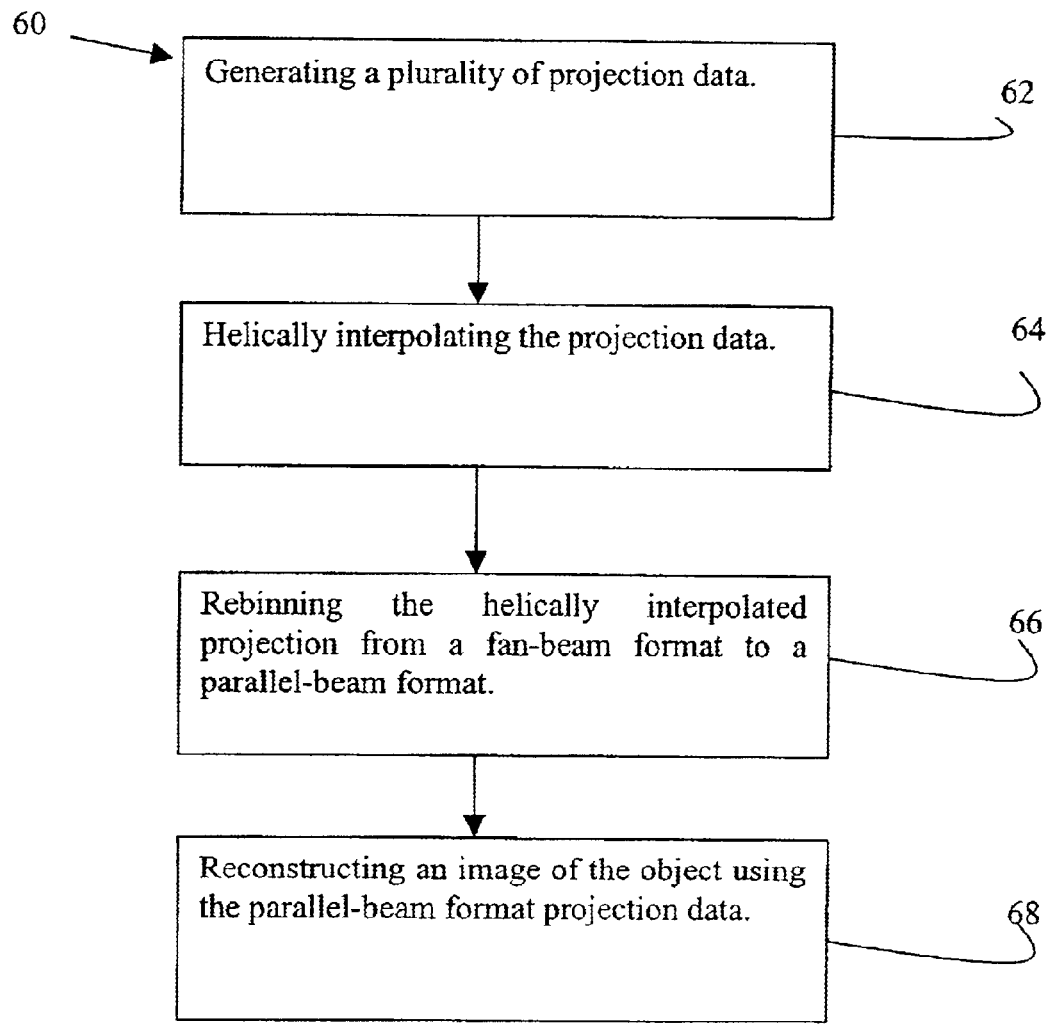
FIG. 3 is a flow chart representative of an exemplary embodiment of a reconstruction algorithm.

FIG. 3 is an exemplary method 60 for reconstructing an image of an object 22. Method 60 includes generating 62 a plurality of projection data, helically interpolating 64 the projection data, rebinning 66 the helically interpolated projection data from a fan-beam format to a parallel-beam format (i.e. fan-parallel rebinning), and reconstructing 68 an image of object 22 using the parallel-beam format projection data.

Performing the projection data rebinning method as described herein provides several advantages. In multi-slice helical reconstruction, projection data from all the detector rows are required to formulate an image, therefore, the rebinning process needs to be carried out for all projection data. For example, for a 16-row detector configuration, the projection data from all 16 detector-rows need to be processed. In use, only a single projection set is rebinned after the weighting and summation process. Further, in the weighting and summation processing, projection data that are one rotation apart are automatically summed to form a single projection at the end of the projection weighting process. For many helical data collected in high-quality (HQ) mode, the number of projections is typically more than one detector rotation. With the additional z-smoothing operation, the number of projections can easily be a factor of 2 to 4 higher than the number of projections in a single rotation. Consequently, the number of projections that are rebinned is significantly reduced when the rebinning is carried out after the weighting step. As described herein, fan-parallel rebinning 68 can be further separated into interpolation in $\beta$ and $\gamma$ directions. In one embodiment, $\beta$ interpolation can be combined with the helical weighting process. In another embodiment, both $\beta$ and $\gamma$ interpolations can be carried out after helical interpolation 66. Since the reconstruction process is linear, the final images produced by both approaches are identical. Method 60 also facilitates reducing the number of projections after rebinning as compared to at least one known fan beam construction. Using the reconstruction method described herein, the minimum angular span of projection is 180 degrees while the angular span for at least one known fan beam projection is 180 degree plus the fan angle. For typical CT scanning geometry, the fan angle is between 50 to 60 degrees. Therefore, there is nearly a 30% saving in the number of views to be filtered and backprojected using the methods described herein compared to at least one known fan beam algorithm.

In one embodiment, fan-parallel rebinning 66 the projection data includes fan-parallel interpolating the projection data in a detector channel direction ($\gamma$) using a higher order interpolation algorithm, such as, but not limited to a $4^{th}$ order LaGrange algorithm. Fan-parallel interpolating the projection data in the detector channel direction ($\gamma$) affects the radial resolution, and therefore facilitates improving high frequency content. Fan-parallel interpolating the projection data also includes interpolating the projection data in a view direction ($\beta$) using an interpolation algorithm different than the detector channel direction algorithm. In one embodiment, fan-parallel interpolating the projection data in a view direction ($\beta$) includes helically interpolating the projection data in a view direction ($\beta$) using a linear interpolation. Fan-parallel interpolating the projection data in the view direction ($\beta$) facilitates improving computational efficiency. In one embodiment, the $\beta$ interpolation is accomplished for all projection samples corresponding to a fixed detector channel ($\gamma$), instead of for a single view across all detector channels, facilitating avoiding the recalculation of interpolation coefficients. For example, if the starting projection is set at $\beta=0$ (for projection dataset starts with a different angle, a simple constant can be added and the entire discussion remains the same), the projection angle for the $k^{th}$ projection is $\beta=k\Delta\beta$. The projection angle, $\beta_p(k)$, for the $k^{th}$ parallel projection at detector angle $\gamma$ is then:

$$\beta_p(k)=k\Delta\beta-\gamma=\Delta\beta(k-\gamma/\Delta\beta) \quad (1)$$

where:

k is a location index;

$\beta$ is a view direction;

$\Delta\beta$ is angular increment between adjacent views in $\beta$; and $\gamma$ is a detector angle along a detector channel direction and $\gamma=0$ for the iso-channel.

In use, $\Delta\beta$ is constant and the index k is an integer, therefore, the only variation in interpolation is due to the fraction part of $\gamma/\Delta\beta$. For a fixed detector channel, the quantity, $\gamma/\Delta\beta$ is constant. Therefore, the interpolation coefficients do not need to be recalculated for all views, but are recalculated once for each detector channel.

In one embodiment, helical weighting 64 and fan-parallel rebinning 66 processing can be combined to reduce the requirement on computation and hardware constraints. For example, fan-parallel rebinning 66 process can be separated into at least two operations, such as, but not limited to, interpolation in $\beta$ and interpolation in $\gamma$. Since these two interpolation steps are independent, the order at which the interpolation steps are carried out is interchangeable. That is, interpolation in $\gamma$ can be produced either prior or post $\beta$ interpolation. For interpolation in $\beta$, the operation can be farther divided into the weighting and the shifting operations. Based on equation (1), the quantity $\gamma/\Delta\beta$ includes an integer part and a fraction part. In use, the fraction part is used to calculate the interpolation coefficients and the integer part facilitates shifting the view index. Therefore, instead of performing the helical weighting and $\beta$ interpolation separately, the helical weights and $\beta$ interpolation weights can be combined. These operations are followed by a shifting operation to account for the integer portion of $\gamma/\Delta\beta$. The fractional part of the $\beta$ interpolation can be done on a subset of the rows. That is, the fractional part of the $\beta$ interpolation is applied only to those detector rows whose helical weights are non-zero for the projection angle. After the projections of the same angle from different detector rows are multiplied by the helical/$\beta$-interpolation weights, these projections can be combined by simple summation to form a single projection. Once the rows have been combined the integer/shifting portion of the interpolation can be accomplished. The shifting operations can be also done on a subset of the rows if it is desirable to perform shifting operation prior to the row combination. The combining of rows and shifting operations are independent, i.e. they can be accomplished in either order. The $\gamma$ interpolation can be done as an independent step or combined into a filtering loop as the first step.

Figure 4:
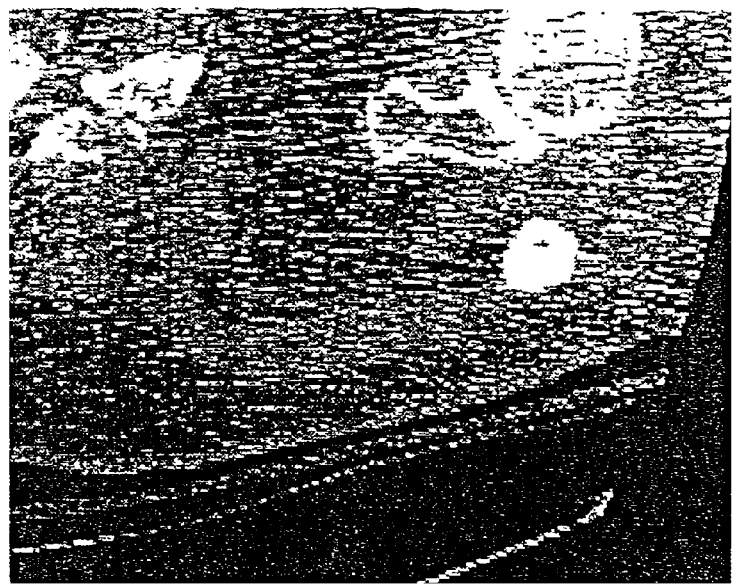
FIG. 4 is patient scan reconstructed with a fan beam algorithm.
Figure 5:
FIG. 5 is a patient scan reconstructed with the parallel reconstruction algorithm described in FIG. 4.
Figure 6:
FIG. 6 is a plurality of maximum intensity projection images.

FIG. 4 is a patient scan reconstructed with a fan beam algorithm. FIG. 5 is the same patient scan shown in FIG. 4 reconstructed with the parallel beam algorithm described herein showing an improvement in noise performance. FIG. 6 is a plurality of maximum intensity projection (MIP) images generated with a fan beam algorithm (top) and the parallel beam algorithm (bottom) described herein showing that a plurality of horizontal strips due to noise modulation shown on the top of FIG. 6 are substantially eliminated as shown in the bottom of FIG. 6 by using the parallel beam algorithm.

To increase scan speed, the number of views that can be collected during one gantry rotation is often limited. Therefore, additional views can be interpolated between the measured views to reduce view aliasing using the adaptive view interpolation method described herein. Using interpolated views, the angular spacing between adjacent views is no longer uniform adding complexities to the fan-parallel rebinning process.

Figure 7:
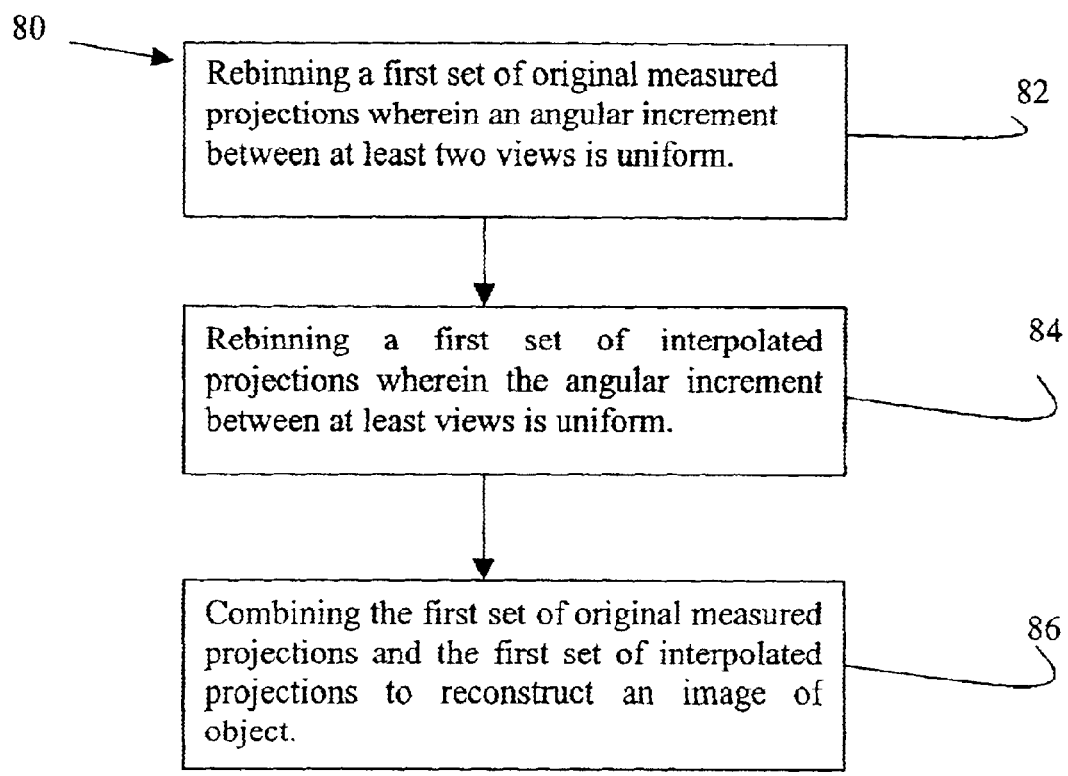
FIG. 7 is a flow chart representative of an exemplary embodiment of a reconstruction algorithm.

FIG. 7 is a method 80 for reconstructing an image of object 22 using interpolated views. Method 80 includes rebinning 82 a first set of original measured projections wherein an angular increment between at least two views is uniform, rebinning 84 a first set of interpolated projections wherein the angular increment between at least two views is uniform, and combining 86 the first set of original measured projections and the first set of interpolated projections to reconstruct an image of object 22. Because the backprojection is a summation process, separate interpolations can then be automatically combined to form the final image.

Method 60 and method 80 facilitate providing approximately twice the noise reduction compared to at least one known fan beam reconstruction method. Further, method 60 and method 80 facilitate eliminating Venetian blinds artifacts in helical 3D formulated images, and facilitate improving coordinate calculation thereby offering hardware savings due to the easier coordinate calculation and removal of the weighting step in the backprojection. For example, computational efficiency is obtained through the combination of projections of different rows and combination of projections that are one rotation apart. Therefore algorithmic development efficiency is obtained from the fact that all the weighting algorithms for fan beam reconstruction do not need to change.

Using a parallel beam reconstruction offers several advantages over using a fan beam reconstruction. For example, parallel beam reconstruction is computationally more efficient than fan beam reconstruction because mapping between the image and projection space is much simpler for the parallel beam geometry. In addition, a location-dependent weighting function used in the fan-beam backprojection is not used in the parallel beam backprojection. Another advantage of the parallel beam backprojection is the improved noise homogeneity that facilitates reducing a plurality of artifacts, such as Venetian Blinds artifacts which are often observed in 3D helical images.

While the invention has been described in terms of various specific embodiments, those skilled in the art will recognize that the invention can be practiced with modification within the spirit and scope of the claims.

What is claimed is:

1. A method for reconstructing an image of an object, said method comprising:
    generating a plurality of projection data;
    helically interpolating the projection data;
    rebinning the helically interpolated projection data from a fan-beam format to a parallel-beam format; and
    reconstructing an image of the object using the parallel-beam format projection data.

2. A method in accordance with claim 1 further comprising:
    pre-processing and calibrating the projection data; and
    filtering and backprojecting the rebinned projection data.

3. A method in accordance with claim 1 wherein said rebinning the helically interpolated projection from a fan-beam format to a parallel-beam format comprises:
    rebinning a first set of original measured projections wherein an angular increment between at least two views is uniform;
    rebinning a first set of interpolated projections wherein the angular increment between at least two views is uniform; and
    combining the first set of original measured projections and the first set of interpolated projections to reconstruct an image of the object.

4. A method in accordance with claim 1 wherein said filtering and backprojecting the rebinned projection data comprises filtering and backprojecting a single rebinned projection data set.

5. A method in accordance with claim 1 wherein said rebinning the projection data comprises fan-parallel interpolating the projection data in a detector channel direction using a higher order interpolation algorithm.

6. A method in accordance with claim 1 wherein said rebinning the projection data comprises fan-parallel interpolating the projection data in a view direction using an interpolation algorithm different than a detector channel direction algorithm.

7. A method in accordance with claim 1 wherein said rebinning the projection data comprises fan-parallel interpolating the projection data in a detector channel direction using a plurality of parallel sample locations defined as:

$$\beta_p(k) = k\Delta\beta - \gamma = \Delta\beta(k - \gamma/\Delta\beta)$$

where:
    k is a location index;
    β is a view direction;
    Δβ is angular increment between adjacent views in β; and
    γ is a detector angle along a detector channel direction and γ=0 for an iso-channel.

8. A method for reconstructing an image of an object, said method comprising:
    generating a plurality of projection data;
    helically interpolating the projection data;
    rebinning a first set of original measured projections wherein an angular increment between at least two views is uniform;
    rebinning a first set of interpolated projections wherein the angular increment between at least two views is uniform; and
    combining the first set of original measured projections and the first set of interpolated projections to reconstruct an image of an object.

9. A method for reconstructing an image of an object, said method comprising:
    rebinning a first set of original measured projections wherein an angular increment between at least two views is uniform;
    rebinning a first set of interpolated projections wherein the angular increment between at least two views is uniform; and
    combining the first set of original measured projections and the first set of interpolated projections to reconstruct an image of an object.

10. A method in accordance with claim 9 further comprising:
    generating a plurality of projection data;
    helically interpolating the projection data; and
    reconstructing an image of the object using the combined projections.

11. A method in accordance with claim 10 wherein said rebinning the projection data comprises fan-parallel interpolating the projection data in a detector channel direction using a higher order interpolation algorithm.

12. A method in accordance with claim 10 wherein said rebinning the projection data comprises fan-parallel interpolating the projection data in a view direction using an interpolation algorithm different than a detector channel direction algorithm.

13. A computed tomographic (CT) imaging system for reconstructing an image of an object, said CT system comprising:
    a radiation source;
    a detector array; and
    a computer coupled to said detector array and said radiation source, said computer is configured to:
        generate a plurality of projection data;
        helically interpolate the projection data;
        rebin the helically interpolated projection data from a fan-beam format to a parallel-beam format; and
        reconstruct an image of the object using the parallel-beam format projection data.

14. A medical imaging system in accordance with claim 13 wherein said computer is further configured to:
    pre-process and calibrate the projection data; and
    filter and backproject the rebinned projection data.

15. A medical imaging system in accordance with claim 13 wherein to rebin the helically interpolated projection data from a fan-beam format to a parallel-beam format said computer is farther configured to:
    rebin a first set of original measured projections wherein an angular increment between at least two views is uniform;
    rebin a first set of interpolated projections wherein the angular increment between at least two views is uniform; and combine the first set of original measured projections and the first set of interpolated projections to reconstruct an image of an object.

16. A medical imaging system in accordance with claim 13 wherein to filter and backproject the rebinned projection data said computer further configured to filter and backproject a single rebinned projection data set.

17. A medical imaging system in accordance with claim 13 wherein to rebin the projection data said computer further configured to fan-parallel interpolate the projection data in a detector channel direction using a higher order interpolation algorithm.

18. A medical imaging system in accordance with claim 13 wherein to rebin the projection data said computer further configured to fan-parallel interpolate the projection data in a view direction using an interpolation algorithm different than a detector channel direction algorithm.

19. A medical imaging system in accordance with claim 13 wherein to rebin the projection data said computer further configured to fan-parallel interpolate the projection data in a detector channel direction using a plurality of parallel sample locations defined as:

$$\beta_p(k) = k\Delta\beta - \gamma = \Delta\beta(k - \gamma/\Delta\beta)$$

where:

k is a location index;

$\beta$ is a view direction;

$\Delta\beta$ is angular increment between adjacent views in $\beta$; and $\gamma$ is a detector angle along a detector channel direction and $\gamma=0$ for an iso-channel.

20. A computed tomographic (CT) imaging system for reconstructing an image of an object, said CT system comprising:

a radiation source;

a detector array; and a computer coupled to said detector array and said radiation source, said computer configured to:

generate a plurality of projection data;

helically interpolate the projection data;

rebin a first set of original measured projections wherein an angular increment between at least two views is uniform;

rebin a first set of interpolated projections wherein the angular increment between at least two views is uniform; and combine the first set of original measured projections and the first set of interpolated projections to reconstruct an image of an object.

21. A computer readable medium encoded with a program executable by a computer for reconstructing an image of an object, said program configured to instruct the computer to:

generate a plurality of projection data;

helically interpolate the projection data;

rebin the helically interpolated projection data from a fan-beam format to a parallel-beam format; and reconstruct an image of the object using the parallel-beam format projection data.

22. A computer readable medium in accordance with claim 21 wherein said program is further configured to:

pre-process and calibrate the projection data; and filter and backproject the rebinned projection data.

23. A computer readable medium in accordance with claim 21 wherein to rebin the helically interpolated projection from a fan-beam format to a parallel-beam format said program is further configured to:

rebin a first set of original measured projections wherein an angular increment between at least two views is uniform;

rebin a first set of interpolated projections wherein the angular increment between at least two views is uniform; and combine the first set of original measured projections and the first set of interpolated projections to reconstruct an image of an object.

24. A computer readable medium in accordance with claim 21 wherein to filter and backproject the rebinned projection data said program is further configured to filter and backproject a single rebinned projection data set.

25. A computer readable medium in accordance with claim 21 wherein to rebin the projection data said program is further configured to fan-parallel interpolate the projection data in a detector channel direction using a higher order interpolation algorithm.

26. A computer readable medium in accordance with claim 21 wherein to rebin the projection data said program is further configured to fan-parallel interpolate the projection data in a view direction using an interpolation algorithm different than a detector channel direction algorithm.

27. A computer readable medium in accordance with claim 21 wherein to rebin the projection data said program is further configured to fan-parallel interpolate the projection data in a detector channel direction using a plurality of parallel sample locations defined as:

$$\beta_p(k) = k\Delta\beta - \gamma = \Delta\beta(k - \gamma/\Delta\beta)$$

where:

k is a location index;

$\beta$ is a view direction;

$\Delta\beta$ is angular increment between adjacent views in $\beta$; and $\gamma$ is a detector angle along a detector channel direction and $\gamma=0$ for an iso-channel.

28. A computer readable medium encoded with a program executable by a computer for reconstructing an image of an object, said program configured to instruct the computer to:

generate a plurality of projection data;

helically interpolate the projection data;

rebin a first set of original measured projections wherein an angular increment between at least two views is uniform;

rebin a first set of interpolated projections wherein the angular increment between at least two views is uniform; and combine the first set of original measured projections and the first set of interpolated projections to reconstruct an image of an object.

29. A method for reconstructing an image of an object, said method comprising:

generating a plurality of projection data;

rebinning the projection data from a fan-beam format to a parallel-beam format, wherein said rebinning comprises:

interpolating the projection data in a view direction $\beta$, wherein said interpolating in the view direction $\beta$ comprises separating the interpolation in a view direction $\beta$ into a fractional weighting operation and a shifting operation; and interpolating the projection data in a detector channel direction $\gamma$.

30. A method in accordance with claim 29 further comprising combining a plurality of helical weights and a plurality of $\beta$ interpolation weights.

31. A method in accordance with claim 29 further comprising performing a β interpolation on a sub-set of detector rows.

32. A method in accordance with claim 29 further comprising combining a plurality of projections acquired from the same angle and from different detector rows to generate a single projection.

33. A method in accordance with claim 29 further comprising performing a shifting interpolation on a subset of detector rows.

34. A method in accordance with claim 29 farther comprising:

combining a plurality of projections acquired from the same angle and from different detector rows; and performing a shifting interpolation on the combined projections.

35. A method in accordance with claim 29 further comprising:

performing a shifting interpolation on a subset of detector rows; and combining the interpolated shifted projections to generate a single projection.

* * * * *

UNITED STATES PATENT AND TRADEMARK OFFICE
CERTIFICATE OF CORRECTION

PATENT NO.   : 6,775,347 B2
DATED        : August 10, 2004
INVENTOR(S)  : Hsieh et al.

It is certified that error appears in the above-identified patent and that said Letters Patent is hereby corrected as shown below:

Column 11,
Line 11, after "accordance with claim 29" delete "farther", and insert therefor -- further --.

Signed and Sealed this

Twenty-second Day of November, 2005

JON W. DUDAS
*Director of the United States Patent and Trademark Office*